US00PP17813P3

(12) United States Plant Patent
Utecht

(10) Patent No.: US PP17,813 P3
(45) Date of Patent: Jun. 19, 2007

(54) ***GERANIUM* PLANT NAMED 'FISRUBY'**

(50) Latin Name: ***Pelargonium peltlatum L'Héritier* (hybrid)**
Varietal Denomination: Fisruby

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 338 days.

(21) Appl. No.: 10/998,669

(22) Filed: Nov. 30, 2004

(65) Prior Publication Data

US 2006/0117448 P1 Jun. 1, 2006

(51) Int. Cl.
*A01H 5/00* (2006.01)

(52) U.S. Cl. ..... Plt./332
(58) Field of Classification Search ..... Plt./332
See application file for complete search history.

(56) References Cited

PUBLICATIONS

German PBR Application No. PEL 1892 filed Jun. 4, 2003 and withdrawn Oct. 5, 2004 (Copy of German Gazettes dated 1) Jul. 15, 2003 —Listing Assigned Application for Protection Number (2 pgs.), 2) May 15, 2004 –Publishing Proposed Variety Denomination (2 pgs), and 3) Nov. 15, 2004—Listing Withdrawal of Application for protection (2 pgs)).

Canadian PBR Application No. 03–3896 filed Nov. 21, 2003 (Copy of Canadian Plant Varieties Journal dated Jan. 2004 Listing Assigned Application Number (2 pgs).

Community Plant Variety Office (CPVO) No. 2004/1250 filed Jul. 5, 2004 (Copy of Official Gazette of the CPVO dated Oct. 15, 2004 Listing Assigned Application Number and Variety Denomination (3 pgs).

Fischer 2005 catalogue offering 'Fisruby' (with shipment of plant material available starting Dec. 2004) (3 pgs).

*Primary Examiner*—Kent Bell
(74) *Attorney, Agent, or Firm*—Foley & Lardner LLP

(57) ABSTRACT

A new and distinct cultivar of *geranium* plant named 'Fisruby', particularly characterized by the combined features of dark red, double flowers; large, semi-spherically shaped inflorescences; deep green foliage with distinct zonation; initially round and bushy, and later medium to long, trailing plant habit; and relatively early spring flowering response.

1 Drawing Sheet

Genus and species of the plant claimed: *Pelargonium peltatum L'Héritier* (hybrid).
Variety denomination: 'Fisruby'.

BACKGROUND OF THE INVENTION

The present invention comprises a new and distinct cultivar of *geranium*, botanically known as *Pelargonium peltatum*, and hereinafter referred to by the cultivar name 'Fisruby'.

'Fisruby' is a product of a planned breeding program which had the objective of creating new ivy *geranium* cultivars with semi-double to double-type flowers, zoned foliage, and about medium sized, well-branched growth habit, in various flower colors.

'Fisruby' originated from a hybridization made by the inventor, Angelika Utecht, in a controlled breeding program in Hillscheid, Germany, in 1998. The female parent was the unpatented plant no. 93-361-15, having red, semi-double flowers, very early beginning of flowering, deep green foliage and vigorous, well-branched plant habit. The male parent of 'Fisruby' was the unpatented hybrid pant no. 94-1418-1, characterized by violet, single-type flowers, leaves with distinct zonation, and about medium tall plant habit.

'Fisruby' was selected as one flowering plant within the progeny of the stated cross by Angelika Utecht in 1999 in a controlled environment in Moncarapacho, Portugal.

The first act of asexual reproduction of 'Fisruby' was accomplished when vegetative cuttings were taken from the initial selection in the fall of 1999 in a controlled environment in Moncarapacho, Portugal, by, or under the supervision of, Angelika Utecht.

Horticultural examination of plants grown from cuttings of the plant initiated in May of 2000 in Hillscheid, Germany, and continuing thereafter, has demonstrated that the combination of characteristics as herein disclosed for 'Fisruby' are firmly fixed and are retained through successive generations of asexual reproduction.

BRIEF SUMMARY OF THE INVENTION

'Fisruby' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fisruby' in combination distinguish *geranium* as a new and distinct cultivar:

1. dark-red, double flowers;
2. large, semi-spherically shaped inflorescence;
3. deep green foliage, leaves with rounded lobes, and distinct zonation;
4. moderately vigorous growth, medium or over sized, trailing plant habit; and
5. relatively early spring flowering response.

Of the many commercial cultivars known to the present inventor, the most similar is the variety 'Fisbarock' (U.S. Plant Pat. No. 12,367).

In comparison to 'Fisbarock', 'Fisruby' has a deeper, purple-red, hue of flower color, distinctly zoned foliage, and somewhat less dense plant habit with longer internodes.

BRIEF DESCRIPTION OF THE DRAWINGS

The accompanying photographic drawing shows typical flower and foliage characteristics of 'Fisruby' with colors being as true as possible with an illustration of this type.

The photographic drawing shows as FIG. 1 a close-up side perspective view of a flowering potted 'Fisruby' with leaves, buds and inflorescences; and as FIG. 2 a side perspective view of a flowering hanging basket of 'Fisruby' with leaves, buds and inflorescences.

DETAILED BOTANICAL DESCRIPTION

Figure 1:
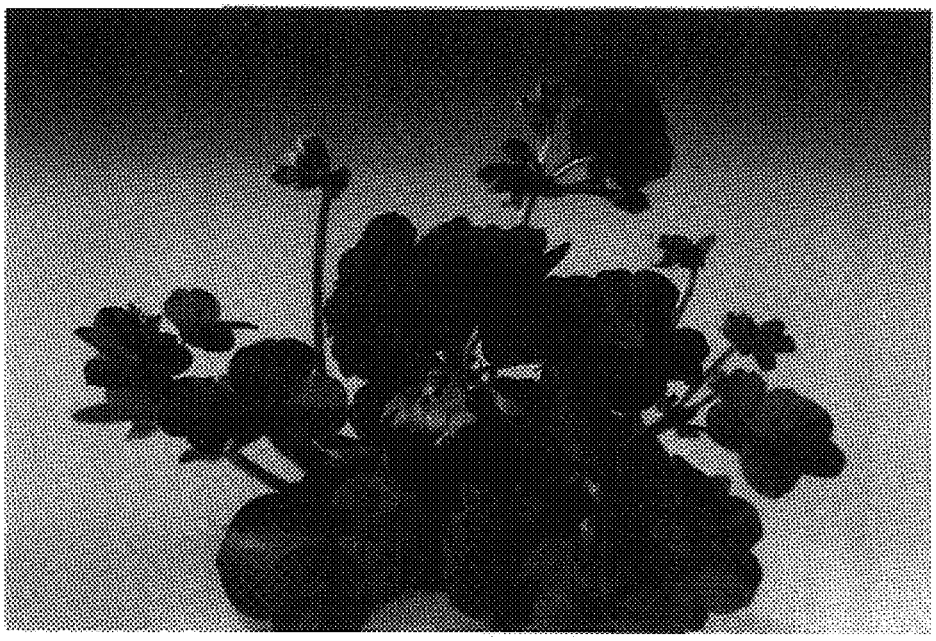
Figure 2:
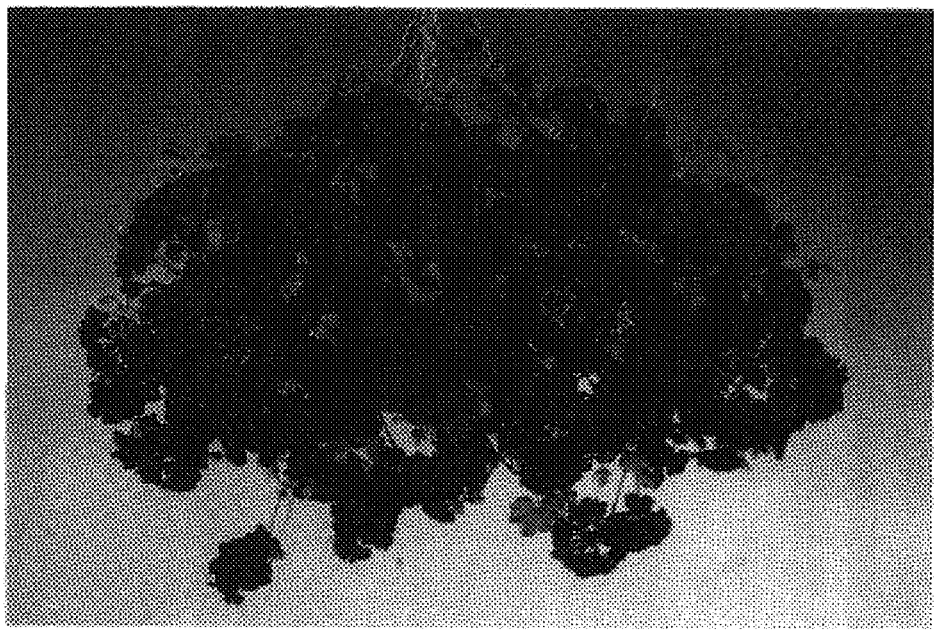

The measurements were taken in Hillscheid, Germany, in mid May 2003, 15 weeks after planting of rooted cuttings. The plants were growing in 14 cm pots; they had been pinched once.

In the following description, color references are made to The Royal Horticultural Society Color Chart. The color values were determined indoors from plants growing in a green-house in May 2003, in Hillscheid, Germany.

Parentage:
- *Male parent*.—Unpatented, hybrid plant no. 94-1418-1.
- *Female parent*.—Unpatented, hybrid plant no. 93-361-15.

Classification: *Pelargonium peltatum L'Héritier* (hybrid).
Propagation: Vegetative cuttings.
Inflorescence:
Umbel:
- *Shape*.—Roughly semi-spherical.
- *Average diameter*.—101 mm.
- *Average depth*.—60–65 mm.
- *Number of flowers per umbel*.—About 8–12.

Peduncle:
- *Peduncle length*.—148 mm.
- *Peduncle diameter*.—3 mm.
- *Peduncle color*.—Light yellow-green, RHS 144 B.

Pedicel:
- *Pedicel length*.—30 mm in length, often with a spur at the lower end.
- *Pedicel diameter*.—2–2.5 mm.
- *Pedicel color*.—Mainly green, RHS 143 A to 143 B, additionally greyed-red stripes may appear, RHS 181B to RHS 181 C.

Corolla:
- *Average length*. —50 mm.
- *Average width*.—43 mm.
- *Depth*.—20 mm.
- *Form*.—Double-type.
- *Shape*.—Oval outline, with the upper petals longer than the rest of petals.

Petaloids:
- *Number of petaloids*.—1–3.
- *Length*.—Variable, ranges from 10 to 15 mm.
- *Width*.—Variable, ranges from 2 to 8 mm.
- *Overall shape*.—Most often narrow and filiform (threadlike), but sometimes nearly petal-shaped (obovate).
- *Apex*.—Acute, or rounded.
- *Base shape*.—Acute or attenuate.
- *Margin*.—Entire.
- *Color of upper petaloids*.—RHS 46 A, base white, RHS 155 D, to pale pink RHS 69 B.
- *Color of lower petaloids*.—RHS 46 A, base white, RHS 155 D, to pale pink RHS 69 B.

Petals:
- *Number of petals*. —15–18.
- *Shape of petals*.—Obovate, base acute, upper end is rounded, margin is entire.
- *Size of petals*.—Upper petals: 28–30 mm long, 18–20 mm wide. Lower petals: 22–23 mm long, 18 mm wide.
- *Color (general tonality from a distance of three meters)*.—Dark red, uniform.
- *Color of upper petals*.—Red, closest to RHS 46 A.
- *Markings of upper petals*.—2 blackish veins (greyed-purple), RHS 187 A.
- *Color of lower petals*.—Red, RHS 46 A.
- *Markings of lower petals*.—None.
- *Color of lower surface of petals*.—Red, from RHS 53 A to 53 B.

Sepals:
- *Number of sepals*.—5.
- *Shape of sepals*.—Linear to lanceolate, acute tip, fused base, surface with fine pubescence, margin entire.
- *Size of sepals*.—12–13 mm long, 5 mm wide for the largest upper sepal, 3 mm in width for the other sepals.
- *Color of sepals*.—Yellow-green, RHS 144 A; largest sepal brown (greyed-purple), RHS 180 B, these values apply to both surfaces.

Bud: (just prior to petals unfolding).
- *Shape*.—Elliptical.
- *Color of sepals*.—Light green, RHS 143 C.
- *Color of petals*.—Deep red, RHS 53 A.
- *Length*.—18 mm.
- *Width*.—9 mm.

Reproductive organs:
- *Androecium*.—5–7 fertile anthers, moderate pollen, orange, RHS 25 A, filaments white, RHS 155 D, to light-pink, RHS 56 A.
- *Gynoecium*.—One pistil, whitish style, RHS 155 D, to red-purple, RHS 65 D, stigma 5–6-lobed stigma, dark greyed-purple, RHS 187 B.
- *Fertility/seed set*.—No seed set observed.

Spring flowering response period: In Hillscheid, Germany, in 2003 plants had on average 1.1 flowers opened 12 weeks after planting of rooted cuttings (pinched plants).

Outdoor flower production: Continuously and moderately rich flowering, the flower count in 2003 in Hillscheid, Germany, indicated about 25 inflorescence per plant in mid May.

Durability: No fading of the flower color; at Hillscheid flowers were not observed to being scorched by the sun, in contrast to many other red to dark-red flowered varieties; fair rain resistance.

Lastingness of the individual flower: About 8 days at 18° C.

Fragrance: None.

Plant:

Foliage:

*Overall shape*.—Ivy-shaped.

*Base shape*.—Cordate base, with open to closed gap between the lowest lobes.

*Apex shape*.—Apex rounded with moderate lobes.

*Margin*.—Entire.

*Texture*.—Upper surface smooth, glossy.

*Size of leaf*.—88 mm wide, about 58 mm long.

*Color of upper surface*.—Deep green, closest to RHS 137 B.

*Color of zonation*.—Brown (greyed-orange), closest to RHS 166 A, distinctness: weak to medium, relatively narrow.

*Color of lower surface*. —Green, RHS 143 B.

*Petiole*.—30–40 mm long, 2.5 mm diameter, light green in color, closest to RHS 143 B.

General appearance and form:

*Stem color*.—Light green, RHS 143 B.

*Internode length*.—3–5 cm.

*Branching pattern*.—6.8 branches on average.

*Size of plants*.—Height: 18.5 cm (15 week-old plants, as described). Diameter: 19 cm (15 week-old plants, as described). Length of plant: 21 cm (15 week-old plants); 75 cm (30 week-old plants, around September 1), measured from the top of the soil (base of the main stem) to the tips of the branches, without inflorescences.

I claim:

1. A new and distinct cultivar of *geranium* plant named 'Fisruby', as described and illustrated herein.

* * * * *